(12) United States Patent
Kalik

(10) Patent No.: US 7,880,621 B2
(45) Date of Patent: Feb. 1, 2011

(54) DISTRACTION ESTIMATOR

(75) Inventor: Steven F. Kalik, Cambridge, MA (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 420 days.

(21) Appl. No.: 11/615,665

(22) Filed: Dec. 22, 2006

(65) Prior Publication Data

US 2008/0154438 A1 Jun. 26, 2008

(51) Int. Cl.
*G08B 23/00* (2006.01)
(52) U.S. Cl. ............... 340/573.1; 340/575; 340/576; 702/182; 701/37; 701/1
(58) Field of Classification Search ............ 701/1; 340/575, 576; 702/182; 180/271
See application file for complete search history.

(56) References Cited

U.S. PATENT DOCUMENTS

| | | | |
|---|---|---|---|
| 5,191,312 A | | 3/1993 | Altmann et al. |
| 5,291,013 A | * | 3/1994 | Nafarrate et al. ........ 250/227.14 |
| 5,648,755 A | | 7/1997 | Yagihashi |
| 6,188,315 B1 | | 2/2001 | Herbert et al. |
| 6,266,589 B1 | | 7/2001 | Boies et al. |
| 6,356,812 B1 | | 3/2002 | Cragun |
| 6,429,789 B1 | | 8/2002 | Kiridena et al. |
| 6,580,973 B2 | | 6/2003 | Leivian et al. |
| 6,580,984 B2 | | 6/2003 | Fecher et al. |
| 6,687,497 B1 | | 2/2004 | Parvulescu et al. |
| 6,727,807 B2 | | 4/2004 | Trajkovic et al. |
| 6,731,925 B2 | | 5/2004 | Naboulsi |
| 6,925,425 B2 | | 8/2005 | Remboski et al. |
| 6,998,972 B2 | | 2/2006 | Geisler et al. |
| 7,039,551 B2 | | 5/2006 | Shu et al. |
| 7,049,941 B2 | | 5/2006 | Rivera-Cintron et al. |
| 7,072,753 B2 | | 7/2006 | Eberle et al. |
| 2003/0096594 A1 | * | 5/2003 | Naboulsi ................ 455/411 |
| 2003/0112132 A1 | | 6/2003 | Trajkovic et al. |
| 2003/0227395 A1 | | 12/2003 | Zeineh |
| 2004/0252027 A1 | * | 12/2004 | Torkkola et al. ........... 340/576 |
| 2005/0030184 A1 | | 2/2005 | Victor |
| 2005/0038573 A1 | | 2/2005 | Goudy |
| 2005/0128092 A1 | * | 6/2005 | Bukman et al. ........... 340/576 |
| 2005/0271280 A1 | * | 12/2005 | Farmer et al. ............ 382/224 |
| 2006/0006990 A1 | | 1/2006 | Obradovich |
| 2008/0114564 A1 | * | 5/2008 | Ihara ..................... 702/158 |

\* cited by examiner

*Primary Examiner*—George A Bugg
*Assistant Examiner*—Ojiako Nwugo
(74) *Attorney, Agent, or Firm*—Gifford, Krass, Sprinkle, Anderson & Citkowski, P.C.

(57) ABSTRACT

Improved apparatus and methods for determining the attention demands on a person are described. An example approach comprises obtaining sensor data representative of the person's environment, detecting sensory objects within the sensor data, and clustering together sensory objects (for example, objects having correlated properties) so as to determine an output number of attention-demanding objects, the output number typically being less than the number of sensory objects in the sensor. An example apparatus may be used to determine the attention demands on a vehicle operator.

6 Claims, 5 Drawing Sheets

DISTRACTION ESTIMATOR

FIELD OF THE INVENTION

The invention relates to vehicle operation, in particular to estimating the attention demands on a driver.

BACKGROUND OF THE INVENTION

Operation of a vehicle places multiple attention demands on the driver, and these attention demands vary according to driving conditions. It would be useful to estimate the attention demands on a driver, for example relative to the attention capacity of the driver. Such estimates would be useful in assisting the driver.

SUMMARY OF THE INVENTION

Embodiments of the present invention provide adaptive models of a driver's attention capabilities, and optionally also of the extravehicular driving environment. Systems are described that allow determination of limits and demands on a driver, and which allow determination of when driver support can be engaged. Prioritization of driver attention is possible, such as disabling an infotainment device. Disablement of electronic devices may be achieved using a separate component receiving an output from an apparatus according to an embodiment of the present invention.

Intra- and extra-vehicular data may be combined to estimate the number of attention-demanding objects that a person, such as a vehicle driver, experiences at a given time. In the case of a driver, attention-demanding objects include other vehicles in the vehicle environment pedestrians, roadside objects, traffic signals, auditory signals from an infotainment device, passenger conversation, cell phone rings, visual display information, and the like. The resulting attention demands may be compared to the driver's maximum ability to deploy attention, or attention capacity, and the current demands of the driver's attention to estimate whether or not the driver can attend to all the required attention demands in the environment. If the situation is determined to be beyond the attention capacity of the driver to monitor it safely, driver support may be provided. For example, additional controllable stimulations (such as a cell phone call) can be delayed or blocked to prevent overload, or other driver support may be engaged.

An example apparatus for determining the attention demands on a driver comprises at least one sensor, providing sensor data representative of the driver environment, and an electronic circuit receiving the sensor data and operable to detect clusterable sensory objects within the sensor data. Clusterable sensory objects may include objects having correlated properties, such as a shared location, shared velocity, and the like. The electronic circuit is operable to cluster together such sensory objects, for example sensory objects having correlated properties, into an output number of clustered objects. The output number of attention-demanding objects provides an improved estimate of the attention demand on the driver, and is typically a lower number than the total number of objects initially detected in the sensor data.

An example method of estimating attention demand on a driver comprises receiving sensor data, identifying sensory objects within the sensor data, clustering sensory objects within the sensor data using correlations between object data (such as one or more co-varying properties), and determining the number of clustered objects in the environment. Optionally, the number of clustered objects may be compared to a threshold value. The threshold value may represent a known or estimated attention capacity of the driver, for example in terms of the number of attention-demanding objects that the driver is capable of attending to at any particular time, also termed the attention capacity of the driver.

DETAILED DESCRIPTION OF THE INVENTION

Figure 1:
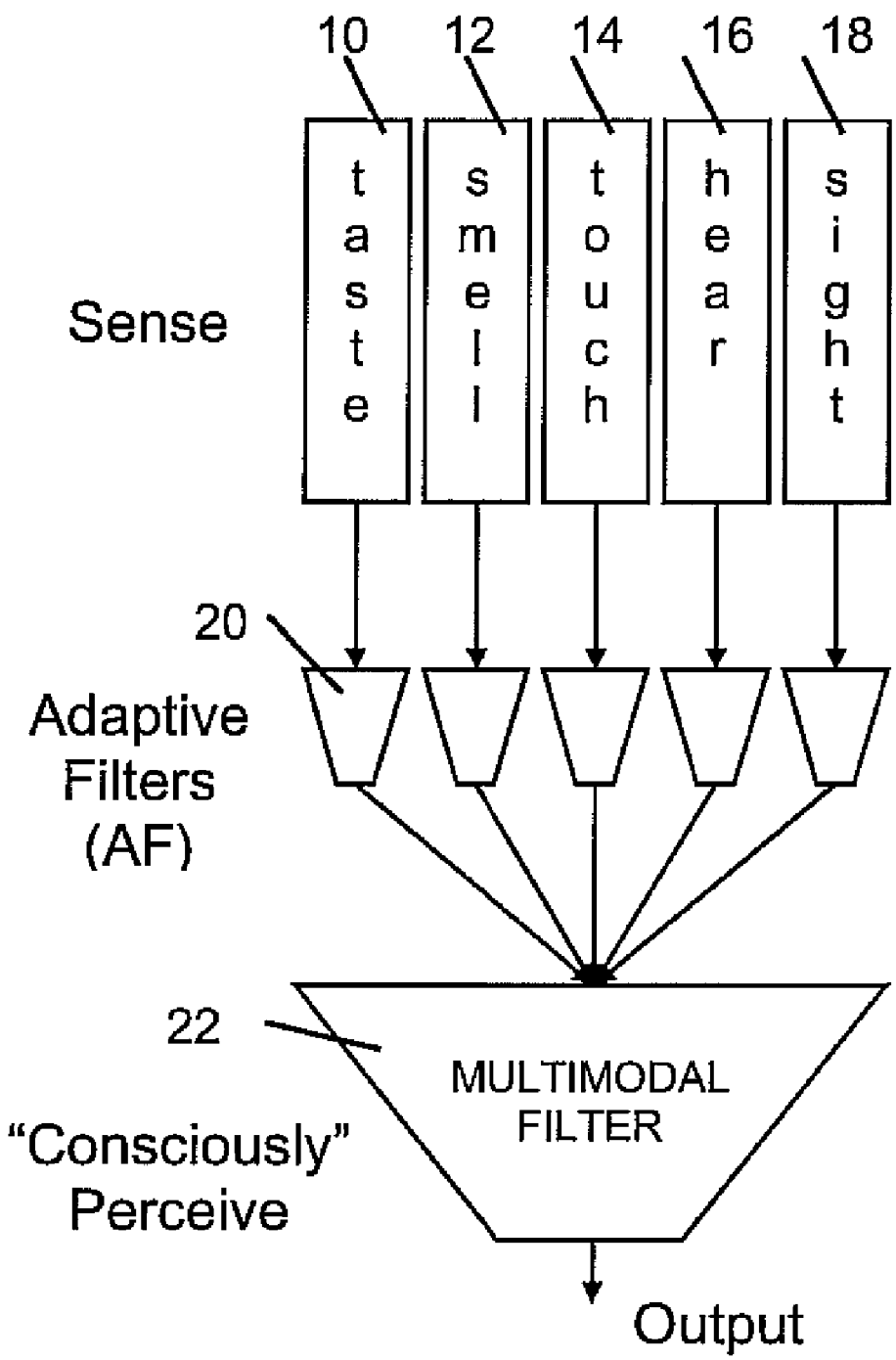
FIG. 1 shows a schematic representative of driver senses, and conscious perception thereof.

Due to the inherent limitations of the human brain and body, a person can only process and respond appropriately to a limited number of attention demands at any one time. However, the exact limits of human capabilities are poorly known, and there are adaptive strategies that humans develop to accommodate these limitations. Hence, it would be useful to determine (1) how many attention demands a particular human can handle at any given time, (2) how many they are handling at that time before they begin to address the driving demands of the extravehicular environment, and (3) how many considerations are required to be handled from the extravehicular environment at a particular time (required attention demands).

The first number sets an upper limit on how many objects a person can attend to without being overwhelmed, or the attention capacity of the person. The second number indicates a number of attention demands to be subtracted from the attention capacity of the person to determine the resources remaining to devote to safe driving, regardless of the extravehicular environment. The final number is related to the number of additional attention-demanding objects introduced by the extravehicular environment. Representative embodiments of the present invention use on-line estimates of these values to determine when it is safe to initiate new tasks, and when it is more appropriate to limit task initiation or performance to maintain safe capacity to respond to the extravehicular driving environment.

In representative examples, apparatus and methods according to the present invention use a model of the human sensory system. Each human sense input includes a number of sensory objects. In a model of human senses, an adaptive filter (AF) is used to "chunk" or cluster these sensory objects together, for example based on correlations between sensory object data. A number of clustered objects is obtained, which is generally less than the number of sensory objects before clustering. This approach provides a better estimate of attention demand on the driver compared with any previous approach.

Each sense receives data including a number of sensory objects. For example, a car in the visual field of view may have attributes such as size, color, and model type, but this combination of data may be clustered as a single clustered object, namely a car. Clustering within each sense reduces the number of objects, and provides a better estimate of the attention demand on the driver. After clustering within each sense, filtering and correlations of the data between senses may further be used to reduce the effective number of clustered objects. For example, some clustered objects may be determined to be largely irrelevant to vehicle operation, for example objects such as multiple trees at the side of a road.

In an apparatus according to an embodiment of the present invention, a number of multimodal filters may be used, for example, to cluster data within and/or between sensor data provided by a plurality of electronic sensors.

Once the estimated number of clustered objects that require driver attention is determined, this number may be compared to a threshold value, for example the maximum attention capacity of the driver. This may be determined individually for the driver, or may be an estimate, for example based on demographic information. After clustering the objects together, an estimate of the driver's present attention allocation can be made. As far as we know, no previous system allows clustering of sensory objects within and/or between the various human sensors.

Hence, an apparatus according to the present invention can determine the limits on a driver's attention, and allow determination of when driver support can be usefully engaged. Driver support may include prioritization of driver attention (such as disabling an infotainment device). However, a separate apparatus may operate to prioritize driver attention, using an output from an apparatus according to the present invention. The number of attention demanding objects a particular person can handle (attention capacity) may be estimated from demographic information (such as age, medical history, and the like), assumed to be a standard amount based on population averages, determined from in-vehicle testing, determined from video-game testing, or otherwise determined.

An apparatus according to an embodiment of the present invention may determine how many attention demands the driver is subjected to at a particular time (the actual attention demand), how many attention demands a driver can handle (attention capacity), and how many attention demands are required to be handled at that time (the required attention demand). Attention demands that are not required, such as cell phone operation, entertainment device operation, gauge information (such as a tachometer), GPS information, and the like, may be disabled for time periods according to the attention demand estimates. The apparatus may further determine when attention demand is at safe enough levels to provide additional attention requirements on the driver, such as gauge readings, other visual information displays, and the like. The apparatus may further provide an alert to a passenger to stop talking.

FIG. 1 is a model of the human sensory system, the model assuming limited resources for attention and perception. The senses here include taste 10, smell 12, touch 14, hearing 16, and sight 18. However, any one or more senses may be modeled according to this approach. In this model, a person makes attention choices within each sense, represented by adaptive filters 20 (using a trapezoid representation). The number of objects is reduced by attention choices of the person, giving a number of objects consciously perceived by the person.

This (or a similar) model can be used to model the limits of human attention. The human senses are replaced by one or more sensors, such as electronic sensors. These may include visual, auditory, vibrational, haptic, chemical analyte (including odor), smoke, or other sensors. In an apparatus according to the present invention, an adaptive filter is used to cluster the sensory objects together within an extravehicular environment model to allow the number of attention-demanding objects to be handled at any moment to be estimated given the structure of data and events in the extra-vehicular environment. Each sensor data stream includes a number of sensory objects. A model of the human sensory system, such as shown in FIG. 1, may be implemented using an electronic circuit, to model the limited resources for attention and perception, to estimate the attention demand on the driver. Sensory objects may be clustered together using correlated properties, such as direction of origin, velocity, position, time-dependence, and the like.

A generalized model may be implemented in an electronic circuit such as a computer. The number of senses considered is arbitrary, and may include electronic sensors similar to natural human senses, or other electronic sensors. Adaptive filters are used to cluster objects within each individual sensor data stream. This clustering process gives a number of clustered objects that is less than or equal to the initial number of sensory objects. Adaptive filters may further operates across senses, detecting correlations between clustered objects with each individual sense, and further reducing the output number of clustered objects. This latter number provides an estimate of the attention demand on the driver that is a great improvement relative to anything described in the prior art.

Figure 2:
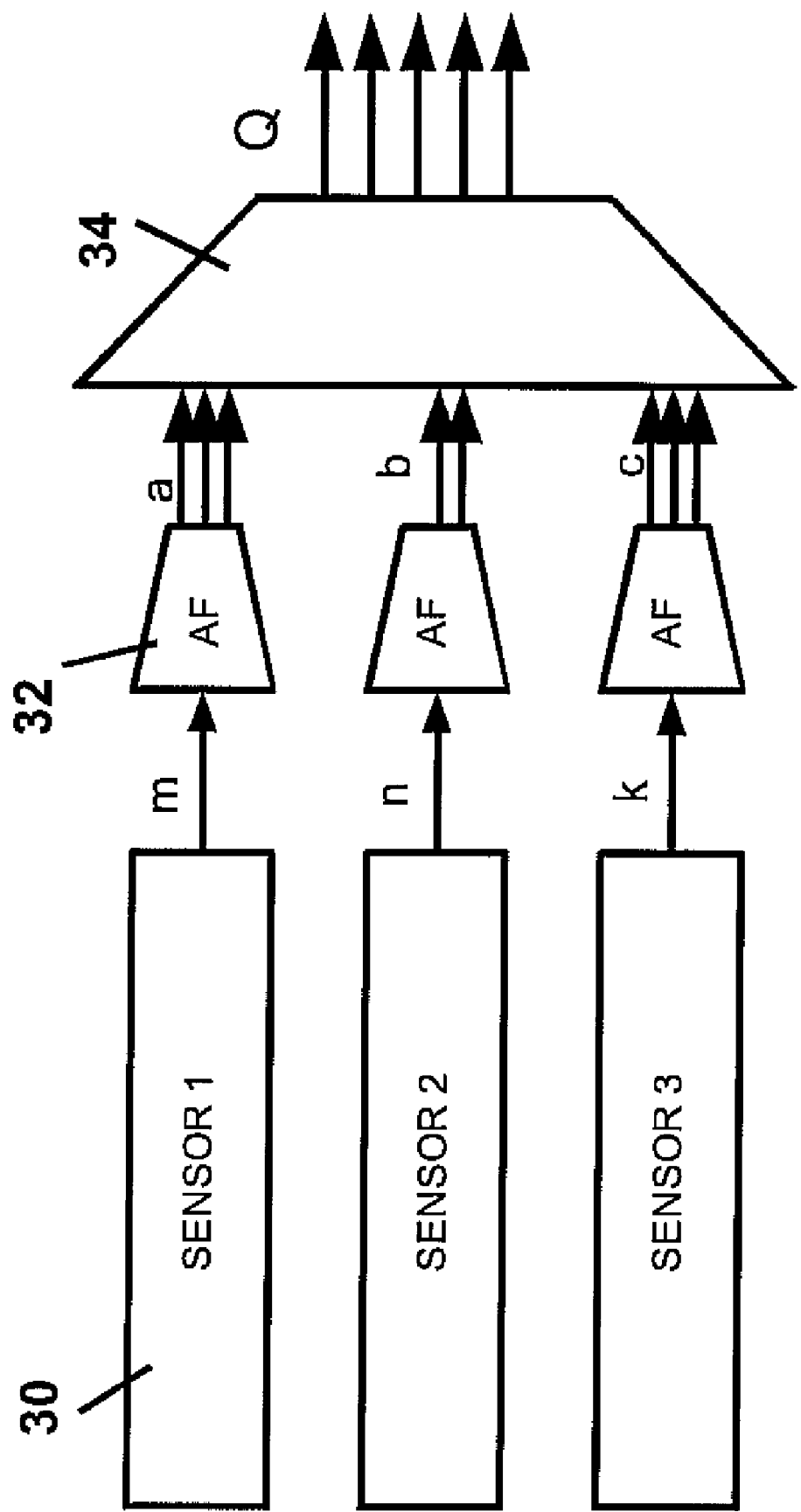
FIG. 2 shows a representation of three sensors, the sensor data being filtered both within and between sensor data streams to provide a reduced number of clustered objects.

FIG. 2 shows a schematic of an apparatus, using a model such as shown in FIG. 1. This may be implemented in an electronic circuit such as an artificial intelligence system or other computer system. In general, N sensors may be used, and for simplicity here N=3. However, N may be greater or less in some situations. The adaptive filters labeled AF may be used to model corresponding adaptive filters (or attention filters) in the human senses.

Each sensor (sensors 1, 2 and 3 in this example), such as sensor 30, provides data including a number of clusterable sensory objects. For example, a car in a field of view may have many attributes, such as size, color, and model type, but all this data may be clustered as a single object (a car). As shown, the number of sensory objects within all sensor data is (m+n+k). Here, sensor data from sensor 1 includes m sensory objects, sensor data from sensor 2 includes n sensory objects, and sensor data from sensor 3 includes k sensory objects. For example, a cell-phone ring may be considered a single auditory sensory object, and music from a radio as another auditory sensory object.

Adaptive filters, such as adaptive filter 32, are used to cluster sensory objects within each sensor data stream. This reduces the effective number of clusters to (a+b+c). For example, a car carrying a bicycle on its roof may be considered a single clustered object, rather than two vehicles. Some clusters may be irrelevant, such as a multiple trees at the side of a road, and may be counted once as a group, or eliminated from the count using a relevance filter. The function of the relevance filter may be provided by the adaptive filters or multimodal filter. Image recognition software may be used to identify visual objects in a visual sensor data stream, or objects otherwise identified from sensed properties.

In this example, the adaptive filters may use correlations between sensory objects within each sensor data stream to cluster the sensory objects. This is followed by correlative clustering across sensor data streams using a multimodal filter 34. For example, the sight and normal sound of a vehicle may be counted only as a single object, and for example perhaps only counted as a single visual object, a single auditory object, or as a single audio-visual object. The output number of attention-demanding objects may then be labeled Q. There may be a plurality of multimodal filters used, for example to cluster objects between data from various electronic sensors. The same sensors and filters used in the present apparatus can be also used to assist driving in other ways, for example through blind spot warnings and the like.

The sensors may correspond to unaugmented human perception (as illustrated in FIG. 1), and may further include the output of electronic sensors, other sensors, or external electronic processing of sensor data. For example, a sensor array may include one or more microphones and/or sensors such as radar (such as Doppler radar), lidar, optical, ultrasound, IR, sonar, and the like.

An apparatus, providing an improved model of the human view of the world, can be implemented in a computer system. The apparatus output (in this case, the output number of attention-demanding objects, Q) may then compared with the person's known attention capacity. If the number of attention-demanding objects is greater than the person's attention capacity, a number of actions may be taken, such as reducing or delaying inputs into the person's awareness (such as the operation of an infotainment device, a cell-phone ring, or an alarm sound).

In other examples, the clustered objects may be weighted. For example, an alarm or cell-phone ring may be assigned a higher numerical value, and Q calculated by summing such numerical values. The person's attention capacity may be represented by a certain value, against which the summed value is compared. A further comparison may be made, for example in terms of the total number of high-value demands against the person's ability to handle a given number of such high value demands. For example, visual objects may be weighted by the spatial distribution of human vision, so that looming objects receive a higher weighting. Dynamic activity, such as relative motion, may also be used for higher weighting.

Figure 3:
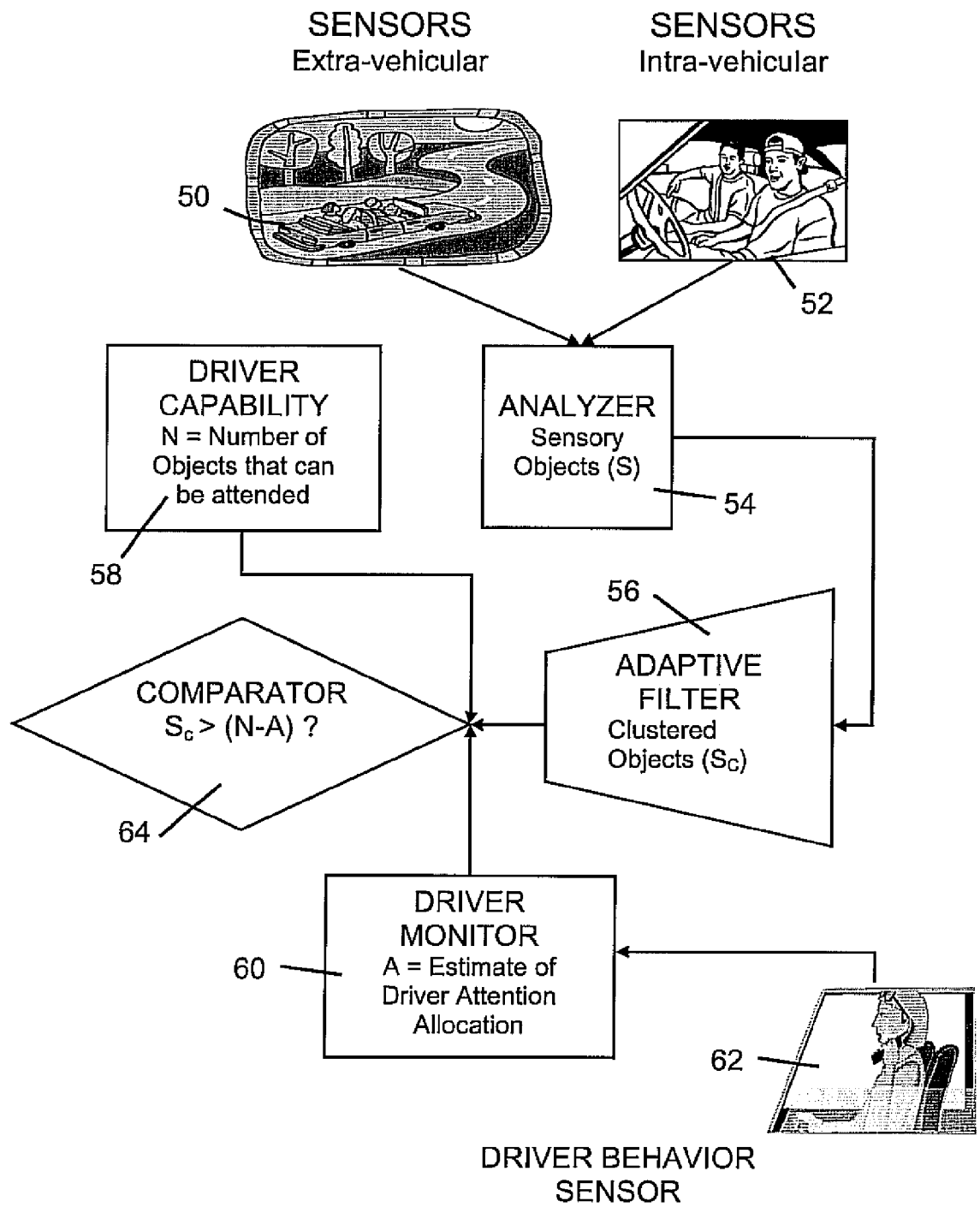
FIG. 3 is a schematic illustrating a comparison of the number of clustered objects, the number of objects that can be attended by the driver, and an estimate of the driver's attention allocation.

FIG. 3 shows a schematic of an approach according to an embodiment of the present invention. Sensors 50 provide sensor data representing the extravehicular environment, including presence of other vehicles, roadside hazards and the like. Sensors 52 provide sensor data representing the intra-vehicular environment, including other passengers, operation of infotainment devices such as radios, cell phone use, and the like. Analyzer 54 identifies objects within the extravehicular and intra-vehicular environments. For example, an image analyzer may identity visual sensory objects from a visual sensor. The number of sensory objects is represented by S. Adaptive filter 56 represents one or more adaptive filters which act to cluster together sensory objects, for example using one or more correlated object properties. The number of clustered objects is represented by $S_C$.

Driver capacity source 58 provides an estimate of the number of objects that can be attended to by the driver (attention capacity). This is represented by N. The attention capacity may be static, or may alternatively be a dynamic value which varies according to conditions, such as driver identity, time of day, driver fatigue, trip length in time or miles, and the like. Driver behavior sensor 62 (for example, which may comprise a visual sensor, eye-tracker, motion sensor, physiological sensor, and the like) monitors the driver behavior, and driver monitor 60 provides an estimate of driver attention allocation. Comparator 64 compares the number of clustered objects $S_C$ (attention-demanding objects) with the attention capacity of the driver (represented by N), subtracted by the estimate of driver attention allocation, represented by A. The driver monitor is optional, and alternatively $S_C$ may be compared with N. In other examples, a driver sensor and driver monitor may be used to estimate the attention capacity of the driver, for example using physiological data relating to alertness.

Values of human attention capacity, human current intra-vehicular attention demands, and current extravehicular attention demands may be determined or estimated. A comparator then allows determination of when (and optionally how) driver support systems should be activated, using such data.

Here, S is the estimated minimum number of sensory objects that demand attention. Sensory objects are clustered together to give ($S_C$) clustered objects. Here, A is an estimate of the driver's present attention allocation. Using the comparison test $S_C > (N-A)$, remedial action may be taken if $S_C$ is greater than $(N-A)$.

This approach can be used for any demanding task, such as vehicle or machine operation, services (such as medical procedures or customer service), or other task.

Figure 4:
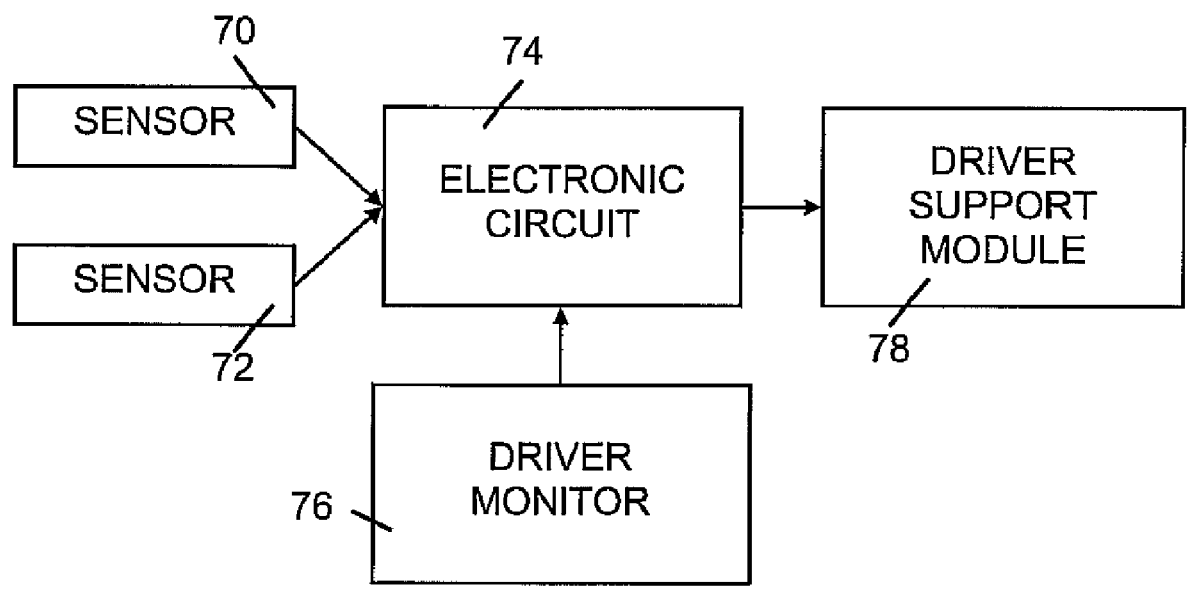
FIG. 4 shows a schematic illustration of an embodiment of the present invention.

FIG. 4 illustrates a schematic diagram in which first and second sensors 70 and 72 respectively input sensor data streams into electronic circuit 74. Driver information is received from driver monitor 78, which may comprise a sensor, database, or combination of information sources. The electronic circuit, which may be a computer, such as an artificial intelligence system, is operable to detect objects within the sensor data, and correlations within and between sensor data. The output of the electronic circuit is fed to a driver support module 78, which may be part of an apparatus according to the present invention, or a separate apparatus. For example, the driver support module may comprise a switch operable to disable cell phone operation, infotainment device operation, or may otherwise provide support to the driver in attending to the environment.

Figure 5:
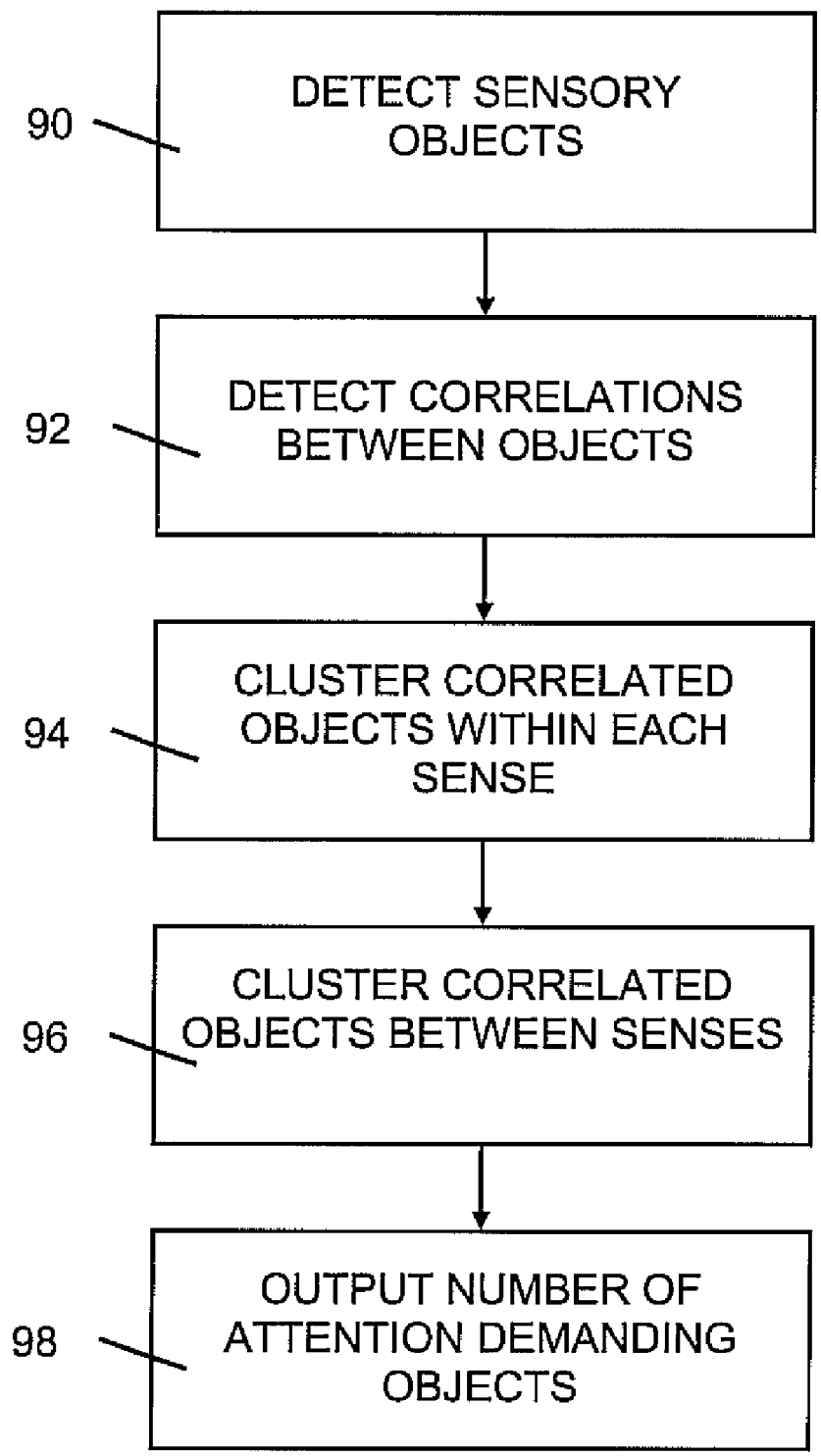
FIG. 5 is a flowchart illustrating a method according to an embodiment of the present invention, the method determining when driver support is helpful to a driver of a vehicle.

FIG. 5 is a flowchart illustrating a simplified operation of a system according to the present invention. Box 90 corresponds to detection of sensory objects within sensor data, for example using a data analyzer. Box 92 corresponds to detecting correlations within sensor data, such as correlated position, direction, velocity, and the like. Box 94 corresponds to clustering of sensory objects into clustered objects. Box 96 corresponds to clustering of object data across sensor data streams (this may be across the equivalent of two or more driver senses, such as hearing and sight, or between two or more different electronic sensors supported by the vehicle). Box 98 corresponds to outputting a number of clustered objects. This may be compared with the attention capacity of the driver.

Embodiments of the present invention allow real-time determination of if a vehicle driver is overloaded. For example, it may be assumed that a driver can handle approximately seven separate objects in the environment, within one sense. However, there may be many more objects detected within the environment. In one approach, statistical data associated with detected objects is examined for correlations, for example common motion within the environment. This correlation allows clustering of clusterable sensory objects into a clustered object, and effectively reduces the apparent demand on the driver from that suggested by a simple count of the number of sensory objects.

Objects may be detected within the environment of the vehicle, and the environment of the operator. These environments overlap but may not be identical. For example driver-only objects might include phone calls, presence of passengers, passenger speech, and the like. Vehicle-only objects may include self-diagnostic data that is not presented to the driver. The presentation of self-diagnostics may be delayed until the attention demand on the driver is reduced, allowing this to be done safely. Embodiments of the present invention allow safety of driver performance to be tracked, without degrading the performance of the driver.

The clustered objects may be weighted according to the sense used by the driver. For example, seven visual clustered objects may be harder for the driver to track than a combination of three visual and four auditory clustered objects. Hence, weightings may be assigned to clustered objects above a certain number within a certain sense of the driver. If the driving conditions are determined to be hazardous, for example through a relatively large number of clustered objects, a number of steps may be taken to assist the driver. For example, a radio or other infotainment device may be turned down or deactivated.

In some cases, clustered objects may include phase data, for example a traffic signal that changes from red to green and then back to red at intervals. The presence of phase data may be used to weight the clustered object. In some cases, the driver may be known to be aware of the surroundings, for example through frequent driving along a certain route. In this case, the presence of a stop sign is known to the driver without a separate observation. Hence, the driver history and familiarity of a route may be used to take certain clustered objects out of the count of objects that place attention demands on the driver. In contrast, a stop light demands attention because of time-dependent (phased) light data, even if a driver is aware of the location.

A vehicle may be equipped with a one or more sensors, such as optical (visual) sensors, acoustic sensors such as microphones, radar, ultrasound, sonar, IR, lidar, other sensors, and the like. Correlations between data within sensor data from a particular sensor allows sensory objects to be clustered, and further inter-sensor correlations across sensor data from different sensors may be used to further reduce the number of clustered objects to an output number of attention-demanding objects. The output number may then be compared with the attention capacity of the driver. Hence, a number of (clusterable sensory) objects are detected in the sensor data, clustered together within and/or between sensor data, and compared with an assumed or adaptive driver attention threshold.

In some examples, an object placing a demand on the driver may be a correlated dynamic cluster. For example, three cars moving together, with the same velocity, adjacent to the driver's vehicle may be clustered together as a single object. However, if one vehicle suddenly accelerates or decelerates, this vehicle may be then counted as a separate object as its behavior is no longer correlated with the other two vehicles. Hence, the model can be dynamic and adaptive to changing surroundings, unlike models used in the prior art.

In a representative example, correlated dynamic clusters are determined by detecting correlations within each data stream, and further by detecting correlations across different data streams. In general, if three data streams have A, B, and C objects therein, the number of correlated dynamic clustered objects Q is less than the sum of A, B, and C due to the presence of correlations. In some examples, the clusters may be combined using set addition, with correlations used to add together into a single set. Correlations may be detected at intervals, for example every 100 milliseconds or some other time as appropriate. With multiple moving objects, correlative filtering within each sense may then be followed by correlative filtering across the senses. The combination of clusterable objects reduces the estimated output number of attention-demanding objects. This approach is a model of a human view of the world, whereas previous approaches have tended to take a machine view of the world.

Context-dependent weighting can also be used to determine the attention demand on the driver. Attention weighting may vary across the visual field, for example objects within the forward direction may be given a greater weight. Looming objects, objects moving in towards the driver's field of view, may also be given an enhanced weight. Unusual objects, such as a running pedestrian, may also be weighted more highly. As an object moves in towards the center of the visual field, more photoreceptors are triggered within the eye, and this may require more attention demand by the driver.

Hence, by modeling the human attention resources and allocation of attention resources, limits and possible overload situations may be identified. There is a possibility of over allocation of attention, where the actual attention demand exceeds the assumed possible attention capacity of the driver. Such a situation may be allowed to continue for a short period, but may then be followed after a certain time period by driver assistance, for example by removing non-required attention demands.

Hence, embodiments of the present invention provide a model to describe the flexible attention allocation of a human, compared with attention demand and attention capacity of the human. A similar model may also be used for non-driving applications, including any situation where it is important that the attention capacity of a person is not exceeded by the actual attention demand. The correlations between and within data sources allow redundant information to be detected, which can then be removed from the count of objects placing demand on the driver by an object clustering process.

In one approach, statistically covarying objects are clustered together into a single (correlated) clustered object. Similarly, non-covarying objects may be considered independent and non-clusterable objects. For clustering, the covariance may be above a threshold covariance value, which may be static or adjusted dynamically according to conditions. The environmental situation may change dynamically, so that clustering of objects may be modified over time. For example, if vehicles accelerate at different rates, the covariance is low. Correlations may be detected between, for example, passenger behavior and the behavior of surrounding vehicles. For example, a passenger may stop talking because of erratic behavior of proximate vehicles. An apparatus according to the present invention hence provides a better estimate of the number of independent sources of data.

In other embodiments, sensor fusion and object detection systems are used to estimate how many separate objects there are to attend to in the combined environments inside and outside of the car. When possible, a system may try to combine objects that can be linked in their behavior, the same way that humans do, to avoid over-estimating the number of objects demanding the attention of the driver. By evaluating the driver's behavior inside the vehicle, a system can then estimate where the driver's attention is directed and how quickly it shifts from one object to the next, to determine when the driver is overwhelmed to attend to everything. This can be used to modify the estimate of driver attention capacity.

System responses to the driver being overwhelmed may include warnings, attempts to direct a driver's attention to places they are overlooking, and preparing vehicular responses in case threats arise from areas being overlooked.

Other applications include aviation and air traffic control applications. In air traffic control applications, there may be extensive covariance of the behavior of airplanes. However, the covariance may be with an intended model of airplane behavior. There may be a time offset between the behavior of different airplanes, however if both airplanes are following the same pattern or model, the attention demand on the air traffic controller is reduced. In this application, objects may be clustered according to time offset behavior that appears to be following the same model with high correlation between statistical properties once the time offset is taken into account. This may be termed oscillatory covariance, where a sum over two functions and normalization factor is used to determine the correlation of two functions $F_1$ and $F_2$.

The amplitude of independence may be compared to the amplitude of covariance to determine if clustering is appropriate. For example in the case of a walking pedestrian, the arm and leg motions of two adjacent persons may have a high degree of oscillatory covariance.

In other applications, chemical detectors may be present, for example for detection of smoke and/or gas, or other analytes. Weighting may be used to enhance the object count associated with smoke detection. Generally such sensory alerts put great attention demands on a driver, or other vehicle or machine operator.

The set of weightings used may be flexible and adaptive according to the environment. Physiological patterns may be detected, for example walking compared with driving. For example, a teeming mass of pedestrians may be grouped together as a single group, but individuals entering the roadway from the sidewalk may give a higher amplitude signal weighted to a higher attention demand.

The physiological state of the driver may also be monitored, for example a tired person may be considered to have a lower attention capacity, and hence able to deal with a smaller number of correlated objects.

Hence, embodiments of the present invention provide improved methods and apparatus for estimating the attention demand on a driver, and the existence of potentially hazardous conditions. These approaches allow better estimates of human limitations within a particular environment, such as driving a vehicle. The improved workload estimate on the driver can then be used to provide assistance to the driver in certain conditions. A video game may be used to determine the maximum attention capacity of a driver, for example for calibrating or otherwise modifying the function of the device.

Applications are not limited to automotive applications, but may further include aviation, robotics, other transportation applications, chemical plant monitoring, equipment operation, and any situation where the attention capacity of a human operator is important for safety.

An example apparatus for estimating the attention demand on an operator of a vehicle comprises a plurality of sensors, each sensor operable to provide sensor data; a plurality of adaptive filters, each adaptive filter operable to receive sensor data from one of the plurality of sensors, each adaptive filter being operable to determine a number of clustered objects within the sensor data; a multimodal adaptive filter operable to cluster objects having correlated properties between sensor data provided by different sensors, the apparatus providing an output number of attention-demanding objects. The plurality of sensors may include at least one visual sensor and at least one auditory sensor.

Sensory object detection within sensor data may include the use of one or more data analyzers. For example, in the case of a visual sensor, an image analyzer may be used to detect visual sensory objects within the visual sensor data. The visual sensory objects may include vehicles, pedestrians, or other objects in a vehicle environment. An adaptive filter associated with the visual sensor may then be operable to cluster visual sensory objects having correlated properties, for example correlated velocities. An auditory sensor may be used to provide auditory sensor data, and a multimodal adaptive filter used to cluster auditory sensory objects within the auditory sensor data with visual sensory objects within the visual sensory data, where the objects have correlated properties, such as direction of origin.

Apparatus according to the present invention may further include an electronic switch operable to disable an electronic device within the vehicle, such as an infotainment device (such as a radio, CD player, DVD player, or internet device), telephone, navigation device (such as a GPS), or other device.

The invention is not restricted to the illustrative examples described above. Examples are not intended as limitations on the scope of the invention. Methods, apparatus, and the like described herein are exemplary and not intended as limitations on the scope of the invention. Changes therein and other uses will occur to those skilled in the art. The scope of the invention is defined by the scope of the claims.

I claim:

1. An apparatus for estimating an attention demand on a person, the person being the operator of a vehicle having a vehicle environment, the apparatus comprising:

a first sensor, providing first sensor data related to the vehicle environment;

a first adaptive filter, receiving the first sensor data and operable to cluster sensory objects within the first sensor data, so as to provide first clustered object data;

a second sensor, providing second sensor data related to the vehicle environment, the first sensor and the second sensor being of different sensor types;

a second adaptive filter, receiving the second sensor data and operable to cluster sensory objects within the second sensor data, so as to provide second clustered object data, the first and second clustered object data including an initial number of clustered objects; and a multimodal adaptive filter, receiving the first and second clustered object data and identifying statistical correlations between clustered objects within the first and second clustered object data, the multimodal adaptive filter providing correlative clustering between the first and second clustered object data so as to obtain an output number of attention-demanding objects as an estimate of the attention demand on the person, the correlative clustering between the first and second clustered object data reducing the output number of attention-demanding objects relative to the initial number of clustered objects.

2. The apparatus of claim 1, further including a comparator operable to compare the output number of attention-demanding objects with an attention capacity of the person.

3. The apparatus of claim 1, wherein the multimodal adaptive filter is operable to cluster sensory objects having a correlated property, the correlated property being selected from a group consisting of position, velocity, and acceleration within the vehicle environment.

4. An apparatus for estimating the attention demand on a person, the person being the operator of a vehicle having a vehicle environment, the apparatus comprising:

a plurality of sensors;

a plurality of adaptive filters, each adaptive filter receiving sensor data related to the vehicle environment from an associated sensor and providing clustered object data related to objects in the vehicle environment, the plurality of adaptive filters providing clustered object data including an initial number of clustered objects; and a multimodal adaptive filter, receiving the clustered object data from the plurality of adaptive filters, the multimodal adaptive filter operable to find statistical correlations between clustered objects originating from different adaptive filters, and to provide further correlative clustering between the clustered objects, the multimodal adaptive filter providing an output number of attention-demanding objects as an estimate of the attention demand on the person, the output number being reduced relative to the initial number of clustered objects by the correlative clustering.

5. The apparatus of claim 4, further including a comparator operable to compare the output number of attention-demanding objects with an attention capacity of the person.

6. The apparatus of claim 4, wherein the multimodal adaptive filter is operable to perform further correlative clustering between clustered object data having a correlated property, the correlated property being selected from a group consisting of position, velocity, and acceleration within the vehicle environment.

* * * * *